United States Patent [19]

Böttcher et al.

[11] Patent Number: 4,617,309

[45] Date of Patent: Oct. 14, 1986

[54] SULFUR-CONTAINING INDOLE DERIVATIVES

[75] Inventors: Henning Böttcher, Darmstadt; Rudolf Gottschlich, Reinheim; Hans-Heinrich Hausberg, Ober-Ramstadt; Christoph Seyfried, Seeheim-Jugenheim; Klaus-Otto Minck, Ober-Ramstadt, all of Fed. Rep. of Germany

[73] Assignee: Merck Patent Gesellschaft mit beschrankter Haftung, Darmstadt, Fed. Rep. of Germany

[21] Appl. No.: 537,621

[22] Filed: Sep. 30, 1983

[30] Foreign Application Priority Data

Sep. 30, 1982 [DE] Fed. Rep. of Germany ....... 3236243

[51] Int. Cl.⁴ .................... C07D 401/12; A61K 31/44
[52] U.S. Cl. .................................... 514/339; 514/338; 546/273; 546/270
[58] Field of Search ................ 546/273, 270; 424/263; 514/338, 339

[56] References Cited

U.S. PATENT DOCUMENTS 3,639,414  2/1972  Archer ................................ 546/273
4,302,589 11/1981  Fanshawe et al. .................. 546/187

Primary Examiner—Jane T. Fan
Attorney, Agent, or Firm—Millen & White

[57] ABSTRACT

Sulfur-containing indole derivatives of the general formula I

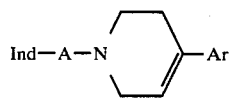

wherein Ind is a 3-indolyl radical which can be substituted once or twice by alkyl, O-alkyl, S-alkyl, SO-alkyl, $SO_2$-alkyl, OH, F, Cl, Br, $CF_3$ and/or CN by a methylenedioxy group, A is $-(CH_2)_n-E-C_mH_{2m}-$ or $-(CH_2)_n-E-C_{m-1}H_{2m-2}CO-$, n is 0 or 1, m is 2, 3 or 4, E is S, SO or $SO_2$ and Ar is a phenyl group which is unsubstituted or substituted once or twice by alkyl, O-alkyl, S-alkyl, SO-alkyl, $SO_2$-alkyl, OH, F, Cl, Br, $CF_3$ and/or CN or by a methylenedioxy group and wherein the alkyl groups each have 1-4 C atoms, and their physiologically acceptable acid addition salts exhibit effects on the central nervous system.

21 Claims, No Drawings

SULFUR-CONTAINING INDOLE DERIVATIVES

This invention relates to new sulfur-containing indole derivatives having valuable pharmacological properties.

SUMMARY OF THE INVENTION

It is an object of this invention to provide new compounds having valuable pharmacological properties. Upon further study of the specification and appended claims, further objects and advantages of this invention will become apparent to those skilled in the art.

These objects have been attained by providing new sulfur-containing indole derivatives of the general formula I

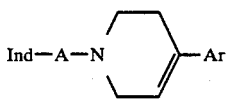

wherein Ind is a 3-indolyl radical which can be substituted once or twice by alkyl, O-alkyl, S-alkyl, SO-alkyl, $SO_2$-alkyl, OH, F, Cl, Br, $CF_3$ and/or CN or by a methylenedioxy group, A is $-(CH_2)_n-E-C_mH_{2m}-$ or $-(CH_2)_n-E-C_{m-1}H_{2m-2}CO-$, n is 0 or 1, m is 2, 3 or 4, E is S, SO or $SO_2$ and Ar is a phenyl group which is unsubstituted or substituted once or twice by alkyl, O-alkyl, S-alkyl, SO-alkyl, $SO_2$-alkyl, OH, F, Cl, Br, $CF_3$ and/or CN or by a methylenedioxy group and wherein the alkyl groups each have 1-4 C atoms, and their physiologically acceptable acid addition salts.

DETAILED DISCUSSION

It was found that the compounds of the formula I and their physiologically acceptable acid addition salts have valuable pharmacological properties. Thus, in particular, they exhibit effects on the central nervous system, especially dopamine-stimulating (anti-parkinsonism) effects. Specifically, the compounds of the formula I induce contralateral turning behaviour in rats with hemiparkinsonism (which may be demonstrated by the method of Ungerstedt et al., Brain Res. 24, (1970), 485–493) and they inhibit the binding of tritiated dopamine agonists and antagonists to striatal receptors (which may be demonstrated by the method of Schwarcz et al., J. Neurochemistry, 34, (1980), 772–778 and Creese et al., European J. Pharmacol., 46, (1977), 377–381). In addition, the compounds inhibit the linguomandibular reflex in the anaesthetised rat (which may be demonstrated by methods derived from Barnett et al., European J. Pharmacol. 21, (1973), 178–182, and from Ilhan et al., European J. Pharmacol. 33, (1975) 61–64). Moreover, analgesic and blood pressure lowering effects occur; thus, the directly measured arterial pressure of unanesthetized rats (method cf. Weeks and Jones, Proc. Soc. Exptl. Biol. Med. 104. (1960), 646–648) is lowered on intragastral application of the compounds.

Thus, compounds of the formula I and their physiologically acceptable acid addition salts can be used as active compounds in medicaments and also as intermediate products for the preparation of other active compounds in medicaments.

The invention relates to the sulfur-containing indole derivatives of the formula I and their physiologically acceptable acid addition salts.

In the radicals Ind and Ar, alkyl is preferably methyl, but is also ethyl, n-propyl, isopropyl, n-butyl, isobutyl, sec.-butyl or tert.-butyl. O-Alkyl is preferably methoxy, but also ethoxy, n-propoxy, isopropoxy, n-butoxy, isobutoxy, sec.-butoxy or tert.-butoxy. S-Alkyl is preferably methylthio, but is also ethylthio, n-propylthio, isopropylthio, n-butylthio, isobutylthio, sec.-butylthio or tert.-butylthio. SO-Alkyl is preferably methylsulfinyl, but is also ethylsulfinyl, n-propylsulfinyl, isopropylsulfinyl, n-butylsulfinyl, isobutylsulfinyl, sec.-butylsulfinyl or tert.-butylsulfinyl. $SO_2$-Alkyl is preferably methylsulfonyl, but is also ethylsulfonyl, n-propylsulfonyl, isopropylsulfonyl, n-butylsulfonyl, isobutylsulfonyl, sec.-butyklsulfonyl or tert.-butylsulfonyl.

The radical Ind is, in particular, an unsubstituted 3-indolyl radical. However, if Ind is a substituted 3-indolyl radical, then it is preferably substituted once, in particular in the 2-, 5- or 6-position. Substitution in the 1-, 4- or 7-position is also possible. Preferred disubstituted 3-indolyl radicals are substituted in the 5,6-positions; disubstitution is also possible in the 1,2-, 1,4-, 1,5-, 1,6-, 1,7-, 2,4-, 2,5-, 2,6-, 2,7-, 4,5-, 4,6-, 4,7-, 5,7- or 6,7-positions. In all these cases the substituents can be identical or different.

Specifically, the preferred substituents in the benzene ring of the Ind radical are methyl, ethyl, methoxy, ethoxy, methylthio, ethylthio, OH, F, Cl, Br, $CF_3$ and CN. Accordingly, some preferred meanings of the Ind radical are 3-indolyl, but also 1-, 2-, 4-, 5-, 6- or 7-methyl-3-indolyl, 1-, 2-, 4-, 5-, 6- or 7-ethyl-3-indolyl, 4-, 5-, 6- or 7-methoxy-3-indolyl, 4-, 5-, 6- or 7-ethoxy-3-indolyl, 4-, 5-, 6- or 7-methylthio-3-indolyl, 4-, 5-, 6- or 7-ethylthio-3-indolyl, 4-, 5-, 6- or 7-methylsulfinyl-3-indolyl, 4-, 5-, 6- or 7-methylsulfonyl-3-indolyl, 4-, 5-, 6- or 7-hydroxy-3-indolyl, 4-, 5-, 6- or 7-fluoro-3-indolyl, 4-, 5-, 6- or 7-chloro-3-indolyl, 4-, 5-, 6- or 7-bromo-3-indolyl, 4-, 5-, 6- or 7-trifluoromethyl-3-indolyl, 4-, 5-, 6- or 7-cyano-3-indolyl, 1,2-, 1,4-, 1,5-, 1,6-, 1,7-, 2,4-, 2,5-, 2,6-, 2,7-, 4,5-, 4,6-, 4,7-, 5,6-, 5,7- or 6,7-dimethyl-3-indolyl, 1-methyl-4-, -5-, -6- or -7-methoxy-3-indolyl, 1-methyl-4-, -5-, -6- or -7-methylthio-3-indolyl, 1-methyl-4-, -5-, -6- or -7-fluoro-3-indolyl, 1-methyl-4-, -5-, -6- or -7-chloro-3-indolyl, 1-methyl-4-, -5-, -6- or -7-bromo-3-indolyl, 1-methyl-4-, -5-, -6- or -7-trifluoromethyl-3-indolyl, 1-methyl-4-, -5-, -6- or -7-cyano-3-indolyl, 2-methyl-4-, -5-, -6- or -7-methoxy-3-indolyl, 2-methyl-4-, -5-, -6- or -7-methylthio-3-indolyl, 2-methyl-4-, -5-, -6- or -7-fluoro-3-indolyl, 2-methyl-4-, -5-, -6- or -7-chloro-3-indolyl, 2-methyl-4-, -5-, -6- or -7-bromo-3-indolyl, 2-methyl-4-, -5-, -6- or -7-trifluoromethyl-3-indolyl, 2-methyl-4-, -5-, -6- or -7-cyano-3-indolyl, 4-methyl-5-fluoro-3-indolyl, 5-fluoro-6- or -7-methyl-3-indolyl, 4-methyl-5-chloro-3-indolyl, 4-chloro-5-methyl-3-indolyl, 5-methyl-6- or -7-chloro-3-indolyl, 5-chloro-6- or -7-methyl-3-indolyl, 4,5-, 4,6-, 4,7-, 5,6-, 5,7- or 6,7-dimethoxy-3-indolyl, 4,5-, 4,6-, 4,7-, 5,6-, 5,7- or 6,7-dichloro-3-indolyl, 4-trifluoromethyl-5-, -6- or -7-chloro-3-indolyl.

The parameter n is preferably 1 and the parameter m is preferably 2. E is preferably S. The group $C_mH_{2m}$ is preferably $-(CH_2)_m-$ and the group $C_{m-1}H_{2m-2}$ is preferably $-(CH_2)_{m-1}-$ (thus both groups are preferably straight-chain).

Accordingly, the radical A is also preferably straight-chain; it is preferably $-CH_2-E-CH_2CH_2-$ or —CH$_2$—E—CH$_2$—CO—, specifically it is preferably —CH$_2$—S—CH$_2$CH$_2$—, —CH$_2$—SO—CH$_2$CH$_2$—, —CH$_2$—SO$_2$—CH$_2$CH$_2$—, —CH$_2$—S—CH$_2$—CO—, —CH$_2$—SO—CH$_2$—CO—, —CH$_2$—SO$_2$—CH$_2$—CO—, but also preferably —E—CH$_2$CH$_2$—, —E—CH$_2$—CO—, —E—(CH$_2$)$_3$—, —E—CH$_2$CH$_2$—CO—, —CH$_2$—E—(CH$_2$)$_3$—, —CH$_2$—E—CH$_2$CH$_2$—CO—, —E—(CH$_2$)$_4$—, —E—(CH$_2$)$_3$—CO—, —CH$_2$—E—(CH$_2$)$_4$— or —CH$_2$—E—(CH$_2$)$_3$—CO—, and specifically is preferably S—CH$_2$CH$_2$—, —SO—CH$_2$CH$_2$—, —SO$_2$—CH$_2$CH$_2$—, —S—CH$_2$—CO—, —SO—CH$_2$—CO—, —SO$_2$—CH$_2$—CO—, —S—(CH$_2$)$_3$—, —SO—(CH$_2$)$_3$—, —SO$_2$—(CH$_2$)$_3$—, —S—CH$_2$CH$_2$—CO—, —SO—CH$_2$CH$_2$—CO—, —SO$_2$—CH$_2$CH$_2$—CO—, —CH$_2$—S—(CH$_2$)$_3$—, —CH$_2$—SO—(CH$_2$)$_3$—, —CH$_2$—SO$_2$—(CH$_2$)$_3$—, —CH$_2$—S—CH$_2$CH$_2$—CO—, —CH$_2$—SO—CH$_2$CH$_2$—CO—, —CH$_2$—SO$_2$—CH$_2$CH$_2$—CO—, —S—(CH$_2$)$_4$—, —SO—(CH$_2$)$_4$—, —SO$_2$—(CH$_2$)$_4$—, —S—(CH$_2$)$_3$—CO—, —SO—(CH$_2$)$_3$—CO—, —SO$_2$—(CH$_2$)$_3$—CO—, —CH$_2$—S—(CH$_2$)$_4$—, —CH$_2$—SO—(CH$_2$)$_4$—, —CH$_2$—SO$_2$—(CH$_2$)$_4$—, —CH$_2$—S—(CH$_2$)$_3$—CO—, —CH$_2$—SO—(CH$_2$)$_3$—CO— or —CH$_2$—SO$_2$—(CH$_2$)$_3$—CO—; but the radical A can also be branched and preferably, for example, be —E—CH(CH$_3$)—, —CH$_2$—E—CH(CH$_3$)—, —E—CH(CH$_3$)—CH$_2$—, —E—CH$_2$—CH(CH$_3$)—, —E—CH(CH$_2$H$_5$)—, —E—CH(CH$_3$)—CO—, —CH$_2$—E—(CH$_3$)—CH$_2$—, —CH$_2$—E—CH$_2$—CH(CH$_3$)—, —CH$_2$—E—CH(C$_2$H$_5$)—, —CH$_2$—E—CH(CH$_3$)—CO—, —E—CH(CH$_3$)—CH$_2$CH$_2$—, —E—CH$_2$—CH(CH$_3$)—CH$_2$—, —E—CH$_2$CH$_2$—CH(CH$_3$)—, —E—CH(C$_2$H$_5$)—CH$_2$—, —E—CH$_2$—CH(C$_2$H$_5$)—, —E—CH(C$_3$H$_7$)—, —E—CH(iso-C$_3$H$_7$)—, —E—CH(CH$_3$)—CH(CH$_3$)—, —E—CH(CH$_3$)—CH$_2$—CO—, —E—CH$_2$—CH(CH$_3$)—CO—, —E—CH(C$_2$H$_5$)—CO—, —CH$_2$—E—CH(CH$_3$)—CH$_2$CH$_2$—, —CH$_2$—E—CH$_2$—CH(CH$_3$)—CH$_2$—, —CH$_2$—E—CH$_2$CH$_2$—CH(CH$_3$)—, —CH$_2$—E—CH(C$_2$H$_5$)—CH$_2$—, —CH$_2$—E—CH$_2$—CH(C$_2$H$_5$)—, —CH$_2$—E—CH(C$_3$H$_7$)—, —CH$_2$—E—CH(isoC$_3$H$_7$)—, —CH$_2$—E—CH(CH$_3$)—CH(CH$_3$)—, —CH$_2$—E—CH(CH$_3$)—CH$_2$—CO—, —CH$_2$E—CH$_2$—CH(CH$_3$)—CO—, —CH$_2$—E—CH(C$_2$H$_5$)—CO—, specifically it is preferably —S—CH(CH$_3$)—, —CH$_2$—S—(CH$_3$)—, —S—CH(CH$_3$)—CH$_2$—, —S—CH$_2$—CH(CH$_3$)—, —S—CH(C$_2$H$_5$)—, S—CH(CH$_3$)—CO—, —CH$_2$—S—CH(CH$_3$)—CH$_2$—, —CH$_2$—S—CH$_2$—CH(CH$_3$)—, —CH$_2$—S—CH(C$_2$H$_5$)—, —CH$_2$—S—CH(CH$_3$)—CO—, —S—CH(CH$_3$)—CH$_2$CH$_2$—, —S—CH$_2$—CH(CH$_3$)—CH$_2$—, —S—CH$_2$CH$_2$—CH(CH$_3$)—, —S—CH(C$_2$H$_5$)—CH$_2$—, —S—CH$_2$CH(C$_2$H$_5$)—, —S—CH(C$_3$H$_7$)—, —S—CH(iso-C$_3$H$_7$)—, —S—CH(CH$_3$)—CH(CH$_3$)—, —S—CH(CH$_3$)—CH$_2$—CO—, —S—CH$_2$—CH(CH$_3$)—CO—, —S—CH(C$_2$H$_5$)—CO—, —CH$_2$—S—CH(CH$_3$)—CH$_2$CH$_2$—, —CH$_2$—S—CH(CH$_3$)—CH$_2$—, —CH$_2$—S—CH$_2$—CH(CH$_3$)—, —CH$_2$—S—CH(C$_2$H$_5$)—CH$_2$—, —CH$_2$—S—CH$_2$—CH(C$_2$H$_5$)—, —CH$_2$—S—CH(C$_3$H$_7$)—, —CH$_2$—S—(CH(isoC$_3$H$_7$)—, —CH$_2$—S—CH(CH$_3$)—CH(CH$_3$)—, —CH$_2$—S—CH(CH$_3$)—CH$_2$—CO—, —CH$_2$—S—CH$_2$—CH(CH$_3$)—CO—, —CH$_2$—S—CH(C$_2$H$_5$)—CO— and the corresponding groups which contain a SO group or a SO$_2$ group in place of the S atom.

The radical Ar is preferably unsubstituted phenyl. If Ar is a substituted phenyl group, it is preferably substituted once. However, it can also be substituted twice, it being possible for the substituents to be identical or different. Preferred substituents on the phenyl group are methyl, F, Cl, Br and trifluoromethyl. Specifically, Ar is preferably phenyl, o-, m- or p-fluorophenyl, o-, m- or p-chlorophenyl, o-, m- or p-bromophenyl, o-, m- or p-tolyl, o-, m- or p-trifluoromethylphenyl, but also, for example, o-, m- or p-ethylphenyl, o-, m- or p-n-propylphenyl, o-, m- or p-isopropylphenyl, o-, m- or p-n-butylphenyl, o-, m- or p-isobutylphenyl, also dihalogenophenyl, such as 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-fluoro-4-chlorophenyl, 2-bromo-4-chlorophenyl; dimethylphenyl, such as 2,3-, 2,4-, 2,5-, 2,6-, 3,4- or 3,5-dimethylphenyl; or methylchlorophenyl, such as 2-methyl-4-chlorophenyl.

Accordingly, the invention relates in particular to those compounds of the formula I in which at least one of the radicals mentioned has one of the meanings indicated above, in particular one of the preferred meanings indicated above. Some preferred groups of compounds can be expressed by the following part formulae Ia to Ik which correspond to the formula I and wherein the radicals and parameters which are not specified have the meaning indicated for formula I, but wherein in Ia, Ind is 3-indolyl, methyl-3-indolyl, dimethyl-3-indolyl, methoxy-3-indolyl, dimethoxy-3-indolyl, hydroxy-3-indolyl, dihydroxy-3-indolyl, fluoro-3-indolyl, chloro-3-indolyl, dichloro-3-indolyl, bromo-3-indolyl, cyano-3-indolyl or methylenedioxy-3-indolyl, the substituents preferably being in the 5- or 6-position; in Ib, Ind is 3-indolyl, 5- or 6-methyl-3-indolyl, 5,6-dimethyl-3-indolyl, 5- or 6-methoxy-3-indolyl, 5,6-dimethoxy-3-indolyl, 5- or 6-hydroxy-3-indolyl or 5-cyano-3-indolyl in Ic, A is —(CH$_2$)$_n$—E—C$_m$H$_{2m}$—;

in Id, m is 2 or 3;

in Ie, E is S or SO;

in If, Ar is phenyl, tolyl, methoxyphenyl, fluorophenyl, chlorophenyl, trifluoromethoxyphenyl or chlorotrifluoromethylphenyl;

in Ig, Ar is phenyl;

in Ih, Ind is 3-indolyl, 5-methoxy-3-indolyl, or 5-hydroxy-3-indolyl, A is —S—CH$_2$CH$_2$—, —S—CH$_2$—CO—, —S—(CH$_2$)$_3$—, —S—CH$_2$CH$_2$—CO—, —CH$_2$—S—CH$_2$CH$_2$—, —CH$_2$—S—CH$_2$—CO—, —CH$_2$—SO—CH$_2$CH$_2$—, —CH$_2$—S—(CH$_2$)$_3$— or —CH$_2$—S—CH$_2$CH$_2$—CO— and Ar is phenyl, tolyl, methoxyphenyl, fluorophenyl, chlorophenyl, trifluoromethylphenyl or chlorotrifluoromethylphenyl;

in Ii, Ind is 3-indolyl, A is —(CH$_2$)$_n$—E—C$_m$H$_{2m}$—, m is 2 or 3 and Ar is phenyl;

in Ij, Ind is 3-indolyl, A is —S—CH$_2$CH$_2$—, —S—(CH$_2$)$_3$—, —CH$_2$—S—CH$_2$CH$_2$—, —CH$_2$SO—CH$_2$CH$_2$— or —CH$_2$—S—(CH$_2$)$_3$ and Ar is phenyl;

in Ik, Ind is 3-indolyl, A is —CH$_2$—E—CH$_2$CH$_2$— or —CH$_2$—E—CH$_2$CO— and Ar is phenyl.

The compounds of the formula I can have one or more asymmetric carbon atoms. Thus they can exist as racemates and, if several asymmetric carbon atoms are present, they can also exist as mixtures of several racemates and in various optically active forms.

The invention also relates to a process for the preparation of the compounds of the formula I and their physiologically acceptable acid addition salts, which is characterised in that a compound of the general formula II

wherein $X^1$ is X or $NH_2$ and X is Cl, Br, I, OH or a reactive functionally modified OH group and Ind and A have the indicated meanings, is reacted with a compound of the general formula III

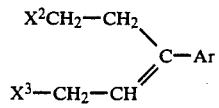

wherein $X^2$ and $X^3$ can be identical or different and, if $X^1$ is $NH_2$, are each X but otherwise are together NH, and Ar has the indicated meaning; or a compound which otherwise corresponds to the formula I but contains, in place of one or more hydrogen atoms, one or more reducible group(s) and/or one or more additional C—C and/or C—N bond(s) is treated with a reducing agent; or a compound which otherwise corresponds to the formula I but contains, in place of one or more hydrogen atoms, one or more group(s) which can be split off solvolytically, is treated with a solvolyzing agent; or a compound of the general formula IV

wherein R is alkyl having 1-4 C atoms, or both radicals R together are also —$(CH_2)_p$— or —$CH_2CH_2OCH_2CH_2$— and p is 4 or 5 and Ind has the indicated meaning is reacted with a thiol of the general formula V

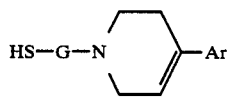

wherein G is —$C_mH_{2m}$— or —$C_{m-1}H_{2m-2}CO$— and m and Ar have the indicated meanings, or one of its salts; or a thiol of the general formula VI

wherein Ind has the indicated meaning, or one of its salts, is reacted with a compound of the general formula VII

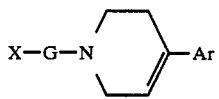

wherein X, G and Ar have the indicated meanings; or a compound of the formula VIII

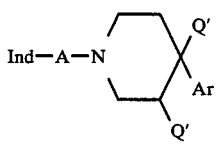

wherein one radical Q' is X, CN or $NH_2$ and the other radical Q' is H and Ind, A, Ar and X have the indicated meanings is treated with an agent which splits off HQ', and/or, where appropriate, in a compound of the formula I, a CO group is reduced to give a $CH_2$ group and/or a thioether group is oxidized to give a SO group or $SO_2$ group, or a SO group is oxidized to give a $SO_2$ group and/or an alkoxy group is cleaved with the formation of an OH group and/or a base of the formula I obtained is converted into one of its physiologically acceptable acid addition salts by treatment with an acid.

The preparation of the compounds of the formula I is otherwise carried out by methods known per se as are described in the literature (for example in the standard works, such as Houben-Weyl, Methoden der Organischen Chemie (Methods of Organic Chemistry), Georg-Thieme-Verlag, Stuttgart; Organic Reactions, John Wiley & Sons, Inc., New York), namely under reaction conditions as are known and suitable for the reactions mentioned. Use can also be made in these preparations of variants known per se which are not mentioned in more detail here.

The starting materials of the formulae II to VIII can, if desired, also be formed in situ in such a manner that they are not isolated from the reaction mixture but are immediately reacted further to give the compounds of the formula I.

The compounds of the formula I, especially the amides I (A=—$(CH_2)_n$—E—$C_{m-1}H_{2m-2}$—CO—), are preferably obtained by reaction of indole derivatives of the formula II with compounds of the formula III.

In the indole derivatives of the formula II, $X^1$ is preferably X; accordingly, in the compounds of the formula III, $X^2$ and $X^3$ together are preferably NH. The radical X is preferably Cl or Br; however, it can also be I, OH or a reactive functionally modified OH group, in particular alkylsulfonyloxy having 1-6 (for example methanesulfonyloxy) or arylsulfonyloxy having 6-10 C atoms (for example benzenesulfonyloxy, p-toluenesulfonyloxy, 1- or 2-naphthalenesulfonyloxy).

Accordingly, the indole derivatives of the formula I can be obtained, in particular, by reaction of the compounds of the formulae Ind—A—Cl or Ind—A—Br with tetrahydropyridine derivatives of the formula III, wherein $X^2$ and $X^3$ together are a NH group (denoted IIIa in the following text).

Some of the compounds of the formulae II and, in particular, III are known; the unknown compounds of the formulae II and III can be easily prepared in analogy to the known compounds. Thus, compounds of the formula II (n=O, E=S) can be obtained, for example, by reaction of 3-mercaptoindoles of the formula Ind—SH (VI) with halogen compounds of the formula Hal—G—$X^1$ (wherein Hal is Cl, Br or I), for example Cl—$CH_2CH_2OH$ or Br—$CH_2COOH$. Compounds of the formula II (n=1, E=S) can be prepared, for example, from Mannich bases of the formula IV (for example gramine) and thiols of the formula HS—G—$X^1$, for example HS—$CH_2CH_2OH$ or HS—$CH_2$—COOH. The sulfoxides and sulfones of the formula II (E=—SO— or —$SO_2$—) are accessible by oxidation of the thioethers (II, E=S).

Primary alcohols of the formula II, wherein the group —A—$X^1$ is a —$(CH_2)_n$—E—$C_{m-1}H_{2m-2}$—$CH_2OH$ group, for example Ind—$CH_2$13 S—$CH_2CH_2OH$ can be obtained, for example, by reduction of the corresponding carboxylic acids or their esters. Treatment with thionyl chloride, hydrogen bromide, phosphorus tribromide or similar halogen compounds provides the corresponding halides of the formula Ind—A—Hal, for example 3-(4-chloro-2-thiabutyl)-indole or 3-(4-bromo-2-thiabutyl)-indole. The corresponding sulfonyloxy compounds can be obtained from the alcohols Ind—A—OH by reaction with the corresponding sulfonyl chlorides.

The iodine compounds of the formula Ind—A—I, for example 3-(4-iodo-2-thiabutyl)indole are obtained, for example, by the action of potassium iodide on the pertinent p-toluenesulfonic esters. The amines of the formula Ind—A—NH$_2$ can be obtained, for example, from the halides with potassium phthalimide or by reduction of the corresponding nitriles.

Most of the piperidine derivatives IIIa are known (compare German Offenlegungsschrift No. 2,060,816) and can be obtained, for example, by reaction of 4-piperidone with organometallic compounds of the formula M—Ar (wherein M is a Li atom or MgHal), subsequent hydrolysis to give the corresponding 4-Ar-4-hydroxypiperidines and, if desired, subsequent dehydration to give 4-Ar-3,4-dehydropiperidines. Compounds of the formula III (X$^2$ and X$^3$ each being X) can be prepared, for example, by reduction of 3-Ar-2-pentene-1,5-dioic acid esters to give 3-Ar-2-pentene-1,5-diols and, if appropriate, subsequent reaction with SOCl$_2$ or PBr$_3$.

The reaction of the compounds II and III takes place by methods as are known from the literature for the alkylation of amines. It is possible to fuse the components together in the absence of a solvent, if appropriate in a closed tube or in an autoclave. However, it is also possible to react the compounds in the presence of an inert solvent. Examples of suitable solvents are hydrocarbons, such as benzene, toluene or xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methylpyrrolidone; nitriles, such as acetonitrile, and, if appropriate, mixtures of these solvents with one another or mixtures with water. The addition of an acid-binding agent, for example an alkali metal or alkaline earth metal hydroxide, carbonate or bicarbonate or another weak acid salt of the alkali metals or alkaline earth metals, preferably of potassium, sodium or calcium, or the addition of an organic base, such as triethylamine, dimethylaniline, pyridine or quinoline or an excess of the amine component Ind-A-NH$_2$ or the piperidine derivative of the formula IIIa can be advantageous. It is possible to prepare the amides of the formula I (A=—(CH$_2$)$_n$—E—C$_{m-1}$H$_{2m-2}$—CO—), for example, from the free carboxylic acids of the formula Ind—(CH$_2$)$_n$—E—C$_{m-1}$H$_{2m-2}$—COOH and tetrahydropyridines of the formula IIIa in the presence of a dehydrating agent, for example carbonyldiimidazole or dicyclohexylcarbodiimide in one of the inert solvents indicated, preferably THF. The reaction time depends on the conditions used and is between a few minutes and 14 days, and the reaction temperature is between about 0° and 150°, normally between 20° and 130°.

Furthermore, it is possible to obtain a compound of the formula I by treating a precursor which, in place of hydrogen atoms, contains one or more reducible group(s) and/or one or more additional C—C and/or C—N bond(s) with reducing agents, preferably at temperatures between −80° and +250° in the presence of at least one inert solvent.

Reducible groups (replaceable by hydrogen) are, in particular, oxygen in a carbonyl group, hydroxyl, aryl-sulfonyloxy (for example p-toluenesulfonyloxy), N-benzenesulfonyl, N-benzyl or O-benzyl).

It is possible in principle to convert compounds which contain only one of the abovementioned groups or additional bonds or those compounds which contain together two or more of the abovementioned groups or additional bonds into a compound of the formula I by reduction. Nascent hydrogen or complex metal hydrides, but also reduction by the method of Wolff-Kishner, is preferably used for this purpose.

Preferred starting materials for the reduction correspond to the formula VIIIa

Ind'—L—Q—Ar'  VIIIa wherein Ind' is a 3-indolyl radical which can be substituted once or twice by alkyl, O-alkyl, S-alkyl, SO-alkyl, SO$_2$-alkyl, OH, F, Cl, Br, CF$_3$, CN and/or O-benzyl or by a methylenedioxy group and/or by an arylsulfonyl group or a benzyl group in the 1-position, L is a —(CH$_2$)$_n$—E—C$_m$H$_{2m}$ chain, but it is possible for one or more —CH$_2$— group(s) in this to be replaced by —CO—, and/or for one or more hydrogen atoms in this to be replaced by OH groups, Q is

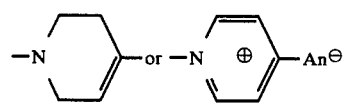

An— is an anion of a strong acid and Ar— is a phenyl group which is unsubstituted or substituted once or twice by alkyl, O-alkyl, S-alkyl, SO-alkyl, SO$_2$-alkyl, OH, F, Cl, Br, CF$_3$, CN and/or O-benzyl or by a methylenedioxy group, but wherein it is not possible at the same time for Ind' to be Ind, L to be A, Q to be

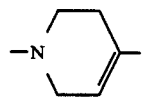

and Ar' to be Ar.

L in the compounds of the formula VIIIa is preferably —(CH$_2$)$_n$—E—CH$_2$—CO—CH$_2$—, —(CH$_2$)$_n$—E—CH$_2$—CO—CH$_2$CH$_2$— or —(CH$_2$)$_n$—E—CH$_2$CH$_2$—CO—CH$_2$—.

Compounds of the formula VIIIa can be prepared, for example, by reaction of 4-Ar'-1,2,3,6-tetrahydropyridine or 4-Ar'-pyridine with a compound of the formula IX Ind'—L—X$^1$  IX wherein Ar', Ind', L and X$^1$ have the meanings indicated above, under the conditions indicated above for the reaction of II with III.

If nascent hydrogen is used as the reducing agent, this can be produced by, for example, treatment of metals with weak acids or with bases. Thus, for example, a mixture of zinc with alkali metal hydroxide solution or of iron with acetic acid can be used.

It is also suitable to use sodium or another alkali metal in an alcohol, such as ethanol, isopropanol, butanol, amyl or isoamyl alcohol or phenol. It is also possible to use an aluminum/nickel alloy in an aqueous alkaline solution, optionally with the addition of ethanol. Sodium amalgam or aluminum amalgam in aqueous alcoholic or aqueous solution are also suitable to produce nascent hydrogen. The reaction can also be carried out in heterogeneous phases, it being preferable to use an aqueous and a benzene or toluene phase.

Moreover, it is possible to use with particular advantage complex metal hydrides, such as $LiAlH_4$, $NaBH_4$, diisobutylaluminum hydride or $NaAl(OCH_2CH_2OCH_3)_2H_2$ and diborane, as the reducing agent, if desired with the addition of catalysts, such as $BF_3$, $AlCl_3$ or $LiBr$. Solvents which are particularly suitable for this purpose are ethers, such as diethyl ether, di-n-butyl ether, THF, dioxane, diglyme or 1,2-dimethoxyethane, and hydrocarbons, such as benzene. For reduction with $NaBH_4$, alcohols, such as methanol or ethanol, but also water and aqueous alcohols, are primarily suitable as the solvent. Reduction by these methods is preferably carried out at temperatures between $-80°$ and $+150°$, in particular between about $0°$ and about $100°$.

It is possible particularly advantageously to reduce —CO— groups in amides (for example those of the formula VIIIa wherein L is a $-(CH_2)_n-E-C_{m-1}H_{2m-2}-CO-$ group) with $LiAlH_4$ in THF at temperatures between about $0°$ and $66°$ to give $CH_2$ groups. During this, arylsulfonyl protective groups located in the 1-position of the indole ring can simultaneously be reductively split off.

It is possible to reduce the pyridinium salts of the formula VIIIa (wherein Q is

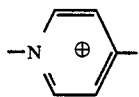

$An^\ominus$ and An is preferably Cl or Br) to give compounds of the formula I, for example, using $NaBH_4$ in water, methanol or ethanol or in mixtures of these solvents, with the addition, if desired, of a base, such as NaOH, at temperatures between about $0°$ and $80°$.

N-Benzyl groups can be reductively split off using sodium in liquid ammonia.

Moreover, it is possible to reduce one or more carbonyl groups to $CH_2$ groups by the method of Wolff-Kishner, for example, by treatment with anhydrous hydrazine in absolute ethanol under pressure at temperatures between about $150°$ and $250°$. Sodium alcoholate is advantageously used as a catalyst. The reduction can also be modified by the method of Huang-Minlon by carrying out the reaction with hydrazine hydrate in a high-boiling solvent which is miscible with water, such as diethylene glycol or triethylene glycol, in the presence of alkali, such as sodium hyroxide. As a rule, the reaction mixture is boiled for about 3-4 hours. The water is then distilled off and the hydrazone formed is decomposed at temperatures up to about $200°$. The Wolff-Kishner reduction can also be carried out with hydrazine in dimethyl sulfoxide at room temperature.

Compounds which otherwise correspond to formula I but, in place of one or more H atoms, contain one or more group(s) which can be split off by solvolysis can be solvolyzed, in particular hydrolyzed, to give compounds of the formula I. The starting materials for the solvolysis can be obtained, for example, by reaction of IIIa with compounds which correspond to the formula II ($X^1=X$) but, in place of one or more H atoms, contain one or more group(s) which can be split off by solvolysis. Thus, 1-acylindole derivatives (corresponding to the formula I but containing an acyl group, preferably an alkanoyl, alkylsulfonyl or arylsulfonyl group each having up to 10 C atoms, such as methane-, benzene- or p-toluenesulfonyl in the 1-position of the Ind radical) can be hydrolyzed to give the corresponding indole derivatives which are unsubstituted in the 1-position of the indole ring, for example, in acid, but better in neutral or alkaline medium at temperatures between $0°$ and $200°$.

Sodium, potassium or calcium hydroxide, sodium or potassium carbonate or ammonia are preferably used as the basic catalysts. The solvents which are preferably chosen are water, lower alcohols, such as methanol or ethanol, ethers, such as THF or dioxane, sulfones, such as tetramethylenesulfone or their mixtures, especially the mixtures containing water. Hydrolysis can even take place just on treatment with water alone, in particular at the boiling point.

Moreover, the indole derivatives of the formula I can be obtained by reaction of the thiols of the formulae V and VI (or their salts) with the compounds of the formulae IV and VII respectively.

Some of the starting materials of the formulae IV to VII are known; those of these starting materials which are unknown can easily be prepared in analogy to the known compounds. Thus, the Mannich bases of the formula IV can be obtained, for example, from indoles of the formula Ind—H, formaldehyde and amines of the formula HN $(R)_2$, and the thiols of the formula V can be obtained from the 4-Ar-tetrahydropyridines of the formula IIIa and of thiol derivatives of the formula HS—G—$X^1$ (intermediate protection of the HS group also being possible). In a similar manner, the tetrahydropyridines of the formula VII are accessible from IIIa and compounds of the formula X—G—$X^1$ (for example chloroacetyl chloride and 1-chloro-2-iodoethane).

Specifically, the reaction of IV with V and of VI with VII takes place in the presence or absence of an inert solvent at temperatures between about $-20°$ and $250°$, preferably between $60°$ and $150°$. Examples of suitable solvents are hydrocarbons, such as benzene, toluene, xylenes or mesitylene; tertiary bases, such as triethylamine; pyridine or picolines; alcohols, such as methanol, ethanol or butanol; glycols and glycol ethers, such as ethylene glycol, diethylene glycol or 2-methoxyethanol; ketones, such as acetone; ethers, such as THF or dioxane; amides, such as DMF or sulfoxides, such as dimethyl sulfoxide. Mixtures of these solvents are also suitable. The thiols of the formulae V and VI are preferably initially converted into the corresponding mercaptides, preferably being converted into the corresponding sodium or potassium mercaptides by reaction with sodium, potassium, sodium or potassium ethylate or sodium or potassium hydride.

Moreover, compounds of the formula I can be obtained by splitting off HQ' from compounds of the formula VIII to form a double bond. According to the definition of Q', this can comprise, for example, splitting off hydrogen halide, water (dehydration), a carboxylic acid or another acid, ammonia or HCN. The starting materials of the formula VIII can be obtained, for example, by reaction of II ($X^1=X$) with a compound of the formula IXa

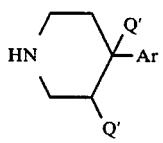

wherein Q' and Ar have the indicated meanings.

If one of the radicals Q' is Hal, this substituent can easily be eliminated under basic reaction conditions. The following can be used as bases: alkali metal hydroxides, alkali metal carbonates, alcoholates, such as, for example, potassium tert.-butylate, amines, such as, for example, dimethylaniline, pyridine, collidine or quinoline; the solvent used is, for example, benzene, toluene, cyclohexane, methanol, dioxane, THF or tert.-butanol. The amines used as bases can also be employed in excess as the solvent. If one of the radicals E is an OH group, then acids, such as acetic acid, hydrochloric acid or mixtures of the two, are preferably used as the agent to split off water. The addition of a solvent (for example water or ethanol) can be advantageous. The elimination of acyl, alkylsulfonyl and alkoxysulfonyloxy or amino radicals can be carried out under similar conditions. An elimination of sulfonic acid radicals, for example mesylates or tosylates, takes place under mild conditions by boiling in DMF or dimethyl sulfoxide with alkali metal carbonates, for example $Li_2CO_3$ or with potassium acetate. Ammonia can be split off by just heating the salts of the corresponding amino compounds (especially the 4-amino derivatives). In a similar manner, HCN can be split off from compounds of the formula VIII (one group Q'=CN) by heating. The elimination of HQ' from VIII generally takes place at temperatures between about 0° and about 250°, preferably between 50° and 200°.

Furthermore, it is possible, if appropriate, to reduce a CO group in a compound of the formula I to a $CH_2$ group, for example with diborane or with a complex metal hydride, such as $LiAlH_4$, in an ether, such as THF, by one of the methods indicated above.

Furthermore, the thioether group in a thioether of the formula I can be oxidized to a SO group or to a $SO_2$ group, or the SO group in a sulfoxide of the formula I can be oxidized to a $SO_2$ group. The thioether or sulfoxide groups to be oxidized can be present in the group A and/or as substituents in the radical Ind and/or in the radical Ar. If the intension is to obtain the sulfoxides, then the oxidation is carried out, for example, with hydrogen peroxide, peracids, such as m-chloroperbenzoic acid, Cr(VI) compounds, such as chromic acid, $KMnO_4$, 1-chlorobenzotriazole, Ce(IV) compounds, such as $(NH_4)_2Ce(NO_3)_6$, negatively substituted aromatic diazonium salts, such as o- or p-nitrophenyldiazonium chloride, or electrolytically under relatively mild conditions and at relatively low tempertures (about −80° to +100°). If, on the other hand, the intention is to obtain the sulfones (from the thioethers or the sulfoxides), then the same oxidizing agents are used under more forcing conditions and/or in excess and, as a rule, at higher temperatures. It is possible in these reactions for the customary inert solvents to be present or absent. Examples of suitable inert solvents are water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, and chlorinated hydrocarbons, such as chloroform or $CCl_4$.

A preferred oxidizing agent is 30% aqueous hydrogen peroxide. On using the calculated amount in solvents such as acetic acid, acetone, methanol, ethanol or aqueous sodium hydroxide solution at temperatures between −20° and 100°, this leads to the sulfoxides, while in excess at higher temperatures, preferably in acetic acid or in a mixture of acetic acid and acetic anhydride, this leads to the sulfones.

Ethers of the formula I in which the radicals Ind and/or Ar are substituted once or twice by O-alkyl can be cleaved by methods which are known from the literature, the corresponding hydroxyl derivatives being produced. For example, the ethers can be cleaved by treatment with HBr or HI in aqueous or acetic acid solution, by heating with Lewis acids, such as $AlCl_3$ or boron trihalides, or by fusing with pyridine or aniline hydrohalides, preferably pyridine hydrochloride, at about 150°–250°.

A base of the formula I which has been obtained can be converted into the relevant acid addition salt using an acid. Acids which provide physiologically acceptable salts are suitable for this reaction. Thus, inorganic acids can be used, for example, sulfuric acid, hydrohalic acids, such as hydrochloric acid or hydrobromic acid, phosphoric acids, such as orthophosphoric acid, nitric acid, sulfamic acid, but also organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemonosulfonic acids and naphthalenedisulfonic acids and lauryl sulfuric acid.

It is possible, if desired, to liberate the free bases of the formula I from their salts by treatment with strong bases, such as sodium or potassium hydroxide or sodium or potassium carbonate.

The invention also relates to the use of the compounds of the formula I and their physiologically acceptable salts for the preparation of pharmaceutical formulations, in particular by non-chemical means. For this purpose, it is possible to convert them into a suitable dosage form together with at least one vehicle or auxiliary and, where appropriate, combined with one or more other active compound(s).

The invention also relates to agents, especially pharmaceutical formulations, containing at least one compound of the formula I and/or one of its physiologically acceptable salts. These formulations can be employed as medicaments in human or veterinary medicine. Suitable vehicles are organic or inorganic substances which are suitable for enteral (for example oral), parenteral or topical administration and which do not react with the new compounds, for example water, vegetable oils, benzyl alcohols, polyethylene glycols, gelatine, carbohydrates, such as lactose or starch, magnesium stearate, talc and vaseline. In particular, tablets, coated tablets, capsules, syrups, liquids, drops or suppositories are used for enteral administration, solutions, preferably oily or aqueous solutions, but also suspensions, emulsions or implants are used for parenteral administration, and ointments, creams or powders are used for topical application. It is also possible to freeze-dry the new compounds and use the lyophilizates obtained, for example, for the preparation of products for injection.

The indicated formulations can be sterilized and/or contain auxiliaries, such as lubricants, preservatives, stabilizers and/or wetting agents, emulsifiers, salts to modify the osmotic pressure, buffer substances, dyes, flavorings and/or aromatic substances. If desired, they can also contain one or more other active compounds, for example one or more vitamins.

The invention also relates to the use of the compounds of the formula I and their physiologically acceptable salts for the therapeutic treatment of the human or animal body and for the control of illnesses, especially of parkinsonism, of extrapyramidal disturbances associated with neutroleptic therapy, of depression and/or psychosis and of side effects of treatment for hypertension (for example with α-methyldopa). The compounds can also be used in endocrinology and gynaecology, or example for the therapy of acromegaly, hypogonadism, secondary amenorrhoea, premenstrual syndrome, undesired puerperal lactation and generally as prolactin inhibitors, also for the therapy of cerebral disturbances (for example migraine) and especially in geriatrics, similar to certain ergot alkaloids.

For these purposes, as a rule, the substances according to the invention are administered in analogy to known and commercially available products (for example bromocriptine and dihydroergocornine), preferably in doses between about 0.2 and 500 mg, in particular between 0.2 and 500 mg per dosage unit. The daily dose is preferably between about 0.001 and 10 mg/kg of body weight. In this context, the low doses (about 0.2 to 1 mg per dosage unit; about 0.001 to 0.005 mg/kg of body weight) are particularly suitable for use as agents for migraine; doses between 10 and 50 mg per dosage unit are preferred for the other indications. More specifically, preferred dosage ranges for specific indications are as follows: parkinsonism 1 to 200, preferably 40 to 100; dyskinesia 40 to 100; psychosis, f.e. chronic schizophrenia 2 to 20; acromegaly 2 to 50 mg per dosage unit. However, the specific dose for each particular patient depends on a wide variety of factors, for example on the efficacy of the specific compound employed, on the age, body weight, general state of health, sex, on the diet, on the timing and mode of administration, on the rate of excretion, and on medicaments used in combination and the severity of the particular disorder to which the therapy is applied. Oral administration is preferred.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

In the examples below, "usual work-up" denotes:

Water is added if necessary, the mixture is extracted with an organic solvent, such as toluene, chloroform or dichloromethane, the phases are separated, the organic phase is dried over sodium sulfate, filtered, evaporated and the product is purified by chromatography and/or crystallization. Temperatures are reported in degrees centigrade. Rf values are obtained by thin layer chromatography using silicagel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 2.26 g of 3-(4-chloro-2-thiabutyl)indole [or 2.70 g of 3-(4-bromo-2-thiabutyl)indole which may be obtained by reaction of gramine with 2-mercaptoethanol to give 3-(4-hydroxy-2-thiabutyl)indole and subsequent reaction with $SOCl_2$ or $PBr_3$] and 1.6 g of 4-phenyl-1,2,3,6-tetrahydropyridine in 10 ml of acetonitrile is stirred at 20° C. for 12 hours, worked up as usual and 3-[4-(4-phenyl-1,2,3,6-tetrahydropyridyl)-2-thiabutyl]indole ("P") of m.p. 109° is obtained.

In analogy, the following are obtained, for example, from the corresponding chloro- or bromothiaalkylindoles:

3-(3-chloro-1-thiapropyl)indole [3-(2-chloroethylthio)indole]
3-(4-chloro-1-thiabutyl)indole
3-(3-chloro-2-methyl-1-thiapropyl)indole
3-(4-chloro-3-methyl-2-thiabutyl)indole
3-(5-chloro-1-thiapentyl)indole
3-(5-chloro-2-thiapentyl)indole
3-(6-chloro-2-thiahexyl)indole
3-(4-chloro-2-thiabutyl)-2-methylindole
3-(4-chloro-2-thiabutyl)-5-methoxyindole
3-(4-chloro-2-thiabutyl)-6-methoxyindole
3-(4-chloro-2-thiabutyl)-4-hydroxyindole
3-(4-chloro-2-thiabutyl)-5-hydroxyindole
3-(4-chloro-2-thiabutyl)-6-hydroxyindole
3-(4-chloro-2-thiabutyl)-5-fluoroindole
3-(4-chloro-2-thiabutyl)-5-chloroindole
3-(4-chloro-2-thiabutyl)-7-bromoindole
3-(4-chloro-2-thiabutyl)-5-cyanoindole
3-(4-chloro-2-thiabutyl)-5,6-methylenedioxyindole
3-(4-chloro-2-thiabutyl)-5,6-dimethylindole
3-(4-chloro-2-thiabutyl)-5,6-dimethoxyindole
3-(4-chloro-2-thiabutyl)-5,6-dichloroindole
or the corresponding sulfoxides and sulfones with the corresponding 4-aryl-1,2,3,6-tetrahydropyridines:
3-[3-(4-phenyl-1,2,3,6-tetrahydropyridyl)-1-thiapropyl]indole, hydrochloride, m.p. 183°–184°
3-[4-(4-phenyl-1,2,3,6-tetrahydropyridyl)-1-thiabutyl]indole, hydrochloride, m.p. 191°–193°
3-[2-methyl-3-(4-phenyl-1,2,3,6-tetrahydropyridyl)-1-thiapropyl]-indole, hydrochloride, decomposition above 205°
3-[3-methyl-4-(4-phenyl-1,2,3,6-tetrahydropyridyl)-2-thiabutyl]indole, m.p. 129°–131°
3-[5-(4-phenyl-1,2,3,6-tetrahydropyridyl)-1-thiapentyl]indole, m.p. 105°–107°

3-[5-(4-phenyl-1,2,3,6-tetrahydropyridyl)-2-thiapentyl]indole, m.p. 132°–134°
3-[6-(4-phenyl-1,2,3,6-tetrahydropyridyl)-2-thiahexyl]indole
3-[4-(4-phenyl-1,2,3,6-tetrahydropyridyl)-2-thiabutyl]-2-methylindole
3-[4-(4-phenyl-1,2,3,6-tetrahydropyridyl)-2-thiabutyl]-5-methoxyindole, hydrochloride, m.p. 182°
3-[4-(4-phenyl-1,2,3,6-tetrahydropyridyl)-2-thiabutyl]-6-methoxyindole
3-[4-(4-phenyl-1,2,3,6-tetrahydropyridyl)-2-thiabutyl]-4-hydroxyindole
3-[4-(4-phenyl-1,2,3,6-tetrahydropyridyl)-2-thiabutyl]-5-hydroxyindole
3-[4-(4-phenyl-1,2,3,6-tetrahydropyridyl)-2-thiabutyl]-6-hydroxyindole
3-[4-(4-phenyl-1,2,3,6-tetrahydropyridyl)-2-thiabutyl]-5-fluoroindole
3-[4-(4-phenyl-1,2,3,6-tetrahydropyridyl)-2-thiabutyl]-5-chloroindole
3-[4-(4-phenyl-1,2,3,6-tetrahydropyridyl)-2-thiabutyl]-7-bromoindole
3-[4-(4-phenyl-1,2,3,6-tetrahydropyridyl)-2-thiabutyl]-5-cyanoindole
3-[4-(4-phenyl-1,2,3,6-tetrahydropyridyl)-2-thiabutyl]-5,6-methylenedioxyindole
3-[4-(4-phenyl-1,2,3,6-tetrahydropyridyl)-2-thiabutyl]-5,6-dimethylindole
3-[4-(4-phenyl-1,2,3,6-tetrahydropyridyl)-2-thiabutyl]-5,6-dimethoxyindole, m.p. 123°–124°
3-[4-(4-phenyl-1,2,3,6-tetrahydropyridyl)-2-thiabutyl]-5,6-dichloroindole
3-[4-(4-o-tolyl-1,2,3,6-tetrahydropyridyl)-2-thiabutyl]indole, hydrochloride, m.p. 176°–178°
3-[4-(4-m-tolyl-1,2,3,6-tetrahydropyridyl)-2-thiabutyl]indole, hydrochloride, m.p. 189°–191°
3-[4-(4-p-tolyl-1,2,3,6-tetrahydropyridyl)-2-thiabutyl]indole
3-[4-(4-o-methoxyphenyl-1,2,3,6-tetrahydropyridyl)-2-thiabutyl]indole
3-[4-(4-m-methoxyphenyl-1,2,3,6-tetrahydropyridyl)-2-thiabutyl]indole
3-[4-(4-p-methoxyphenyl-1,2,3,6-tetrahydropyridyl)-2-thiabutyl]indole, hydrochloride, m.p. 198°
3-[4-(4-o-hydroxyphenyl-1,2,3,6-tetrahydropyridyl)-2-thiabutyl]indole
3-[4-(4-m-hydroxyphenyl-1,2,3,6-tetrahydropyridyl)-2-thiabutyl]indole
3-[4-(4-p-hydroxyphenyl-1,2,3,6-tetrahydropyridyl)-2-thiabutyl]indole
3-[4-(4-o-fluorophenyl-1,2,3,6-tetrahydropyridyl)-2-thiabutyl]indole
3-[4-(4-m-fluorophenyl-1,2,3,6-tetrahydropyridyl)-2-thiabutyl]indole
3-[4-(4-p-fluorophenyl-1,2,3,6-tetrahydropyridyl)-2-thiabutyl]indole, hydrochloride, m.p. 209°
3-[4-(4-o-chlorophenyl-1,2,3,6-tetrahydropyridyl)-2-thiabutyl]indole
3-[4-(4-m-chlorophenyl-1,2,3,6-tetrahydropyridyl)-2-thiabutyl]indole
3-[4-(4-p-chlorophenyl-1,2,3,6-tetrahydropyridyl)-2-thiabutyl]indole
3-[4-(4-p-bromophenyl-1,2,3,6-tetrahydropyridyl)-2-thiabutyl]indole
3-[4-(4-m-trifluoromethylphenyl-1,2,3,6-tetrahydropyridyl)-2-thiabutyl]indole, hydrochloride, m.p. 166°–167°
3-[4-(4-p-cyanophenyl-1,2,3,6-tetrahydropyridyl)-2-thiabutyl]indole
3-[4-(4-(3,4methylenedioxyphenyl)-1,2,3,6-tetrahydropyridyl)-2-thiabutyl]indole
3-[4-(4-(4-chloro-3-trifluoromethylphenyl)-1,2,3,6-tetrahydropyridyl)-2-thiabutyl]indole, hydrochloride, m.p. 210°–211°
3-[4-(4-phenyl-1,2,3,6-tetrahydropyridyl)-2-thiabutyl]indole S-oxide, m.p. 144°–146°
3-[4-(4-phenyl-1,2,3,6-tetrahydropyridyl)-2-thiabutyl]indole, S,S-dioxide.

EXAMPLE 2

A mixture of 4.61 g of 3-(4-p-toluenesulfonyloxy-2-thiabutyl)indole and 3.18 g of 4-phenyl-1,2,3,6-tetrahydropyridine is heated to 130°. After the exothermic reaction is complete and the mixture has cooled down, the usual work-up is carried out and "P" of m.p. 109° is obtained.

In analogy, the following are obtained from the corresponding tosylates:
3-[4-(4-phenyl-1,2,3,6-tetrahydropyridyl)-2-thiabutyl]-5-butylindole
3-[4-(4-phenyl-1,2,3,6-tetrahydropyridyl)-2-thiabutyl]-5-ethoxyindole
3-[4-(4-phenyl-1,2,3,6-tetrahydropyridyl)-2-thiabutyl]-5-butoxyindole
3-[4-(4-phenyl-1,2,3,6-tetrahydropyridyl)-2-thiabutyl]-5-methylthioindole
3-[4-(4-phenyl-1,2,3,6-tetrahydropyridyl)-2-thiabutyl]-5-butylthioindole
3-[4-(4-phenyl-1,2,3,6-tetrahydropyridyl)-2-thiabutyl]-5-methylsulfinylindole
3-[4-(4-phenyl-1,2,3,6-tetrahydropyridyl)-2-thiabutyl]-5-methylsulfonylindole.

EXAMPLE 3

3.17 g of 3-(4-iodo-2-thiabutyl)indole, 1.59 g of 4-phenyl-1,2,3,6-tetrahydropyridine and 1.5 g of anhydrous potassium carbonate in 25 ml of n-butanol are boiled with stirring for 2 hours, allowed to cool down and worked up as usual, "P" of m.p. 109° being obtained.

In analogy, the following are obtained with the corresponding 4-Ar-1,2,3,6-tetrahydropyridines:
3-[4-(4-p-butoxyphenyl-1,2,3,6-tetrahydropyridyl)-2-thiabutyl]indole
3-[4-(4-p-methylthiophenyl-1,2,3,6-tetrahydropyridyl)-2-thiabutyl]indole
3-[4-(4-p-butylthiophenyl-1,2,3,6-tetrahydropyridyl)-2-thiabutyl]indole
3-[4-(4-p-methylsulfinylphenyl-1,2,3,6-tetrahydropyridyl)-2-thiabutyl]indole
3-[4-(4-p-methylsulfonylphenyl-1,2,3,6-tetrahydropyridyl)-2-thiabutyl]indole.

EXAMPLE 4

16.2 g of carbonyldiimidazole are added to a solution of 22.1 g of 4-(3-indolyl)-3-thiabutyric acid (which may be obtained from gramine and thioglycolic acid) in 100 ml of THF, the mixture is stirred at 20° for one hour and then a solution of 15.9 g of 4-phenyl-1,2,3,6-tetrahydropyridine in 50 ml of THF is added. The mixture is stirred at 20° C. for 16 hours, worked up as usual and 3-[4-oxo-4-(4-phenyl-1,2,3,6-tetrahydropyridyl)-2-thiabutyl]indole of m.p. 122°–125° is obtained.

In analogy, for example, the following are obtained from the corresponding carboxylic acids:

3-(3-indolyl)-3-thiapropionic acid (3-indolylthioacetic acid)
4-(3-indolyl)-3-thiabutyric acid
3-(3-indolyl)-2-methyl-3-thiapropionic acid
4-(3-indolyl)-4-thiabutyric acid
4-(3-indolyl)-2-methyl-3-thiabutyric acid
5-(3-indolyl)-4-thiavaleric acid
5-(3-indolyl)-5-thiavaleric acid
6-(3-indolyl)-5-thiacaproic acid
4-(2-methylindolyl)-3-thiabutyric acid
4-(5-methoxyindolyl)-3-thiabutyric acid
4-(6-methoxyindolyl)-3-thiabutyric acid
4-(4-hydroxyindolyl)-3-thiabutyric acid
4-(5-hydroxyindolyl)-3-thiabutyric acid
4-(6-hydroxyindolyl)-3-thiabutyric acid
4-(5-fluoroindolyl)-3-thiabutyric acid
4-(5-chloroindolyl)-3-thiabutyric acid
4-(7-bromoindolyl)-3-thiabutyric acid
4-(5-cyanoindolyl)-3-thiabutyric acid
4-(5,6-methylenedioxyindolyl)-3-thiabutyric acid
4-(5,6-dimethylindolyl)-3-thiabutyric acid
4-(5,6-dimethoxyindolyl)-3-thiabutyric acid
4-(5,6-dichloroindolyl)-3-thiabutyric acid
or the corresponding sulfoxides and sulfones with the corresponding 4-aryl-1,2,3,6-tetrahydropyridines:
3-[3-oxo-3-(4-phenyl-1,2,3,6-tetrahydropyridyl)-1-thiapropyl]indole, Rf 0.5 (ethyl acetate)
3-[4-oxo-4-(4-phenyl-1,2,3,6-tetrahydropyridyl)-1-thiabutyl]indole, Rf 0.5 (ethyl acetate)
3-[2-methyl-3-oxo-3-(4-phenyl)-1,2,3,6-tetrahydropyridyl)-1-thiapropyl]indole, Rf 0.5 (ethyl acetate)
3-[3-methyl-4-oxo-4-(4-phenyl-1,2,3,6-tetrahydropyridyl)-1-thiabutyl]indole, Rf 0.75 ($CH_2Cl_2/CH_3OH$ 9:1)
3-[5-oxo-5-(4-phenyl-1,2,3,6-tetrahydropyridyl)-1-thiapentyl]indole, Rf 0.6 (ethyl acetate)
3-[5-oxo-5-(4-phenyl-1,2,3,6-tetrahydropyridyl)-2-thiapentyl]indole, m.p. 133°–134°
3-[6-oxo-6-(4-phenyl-1,2,3,6-tetrahydropyridyl)-2-thiahexyl]indole
3-[4-oxo-4-(4-phenyl-1,2,3,6-tetrahydropyridyl)-2-thiabutyl]-2-methylindole
3-[4-oxo-4-(4-phenyl-1,2,3,6-tetrahydropyridyl)-2-thiabutyl]-5-methoxyindole, Rf 0.78 ($CH_2Cl_2$/methanol/ethyl acetate 7:2:1)
3-[4-oxo-4-(4-phenyl-1,2,3,6-tetrahydropyridyl)-2-thiabutyl]-6-methoxyindole
4-[4-oxo-4-(4-phenyl-1,2,3,6-tetrahydropyridyl)-2-thiabutyl]-4-hydroxyindole
3-[4-oxo-4-(4-phenyl-1,2,3,6-tetrahydropyridyl)-2-thiabutyl]-5-hydroxyindole
3-[4-oxo-4-(4-phenyl-1,2,3,6-tetrahydropyridyl)-2-thiabutyl]-6-hydroxyindole
3-[4-oxo-4-(4-phenyl-1,2,3,6-tetrahydropyridyl)-2-thiabutyl]-5-fluoroindole
3-[4-oxo-4-(4-phenyl-1,2,3,6-tetrahydropyridyl)-2-thiabutyl]-5-chloroindole
3-[4-oxo-4-(4-phenyl-1,2,3,6-tetrahydropyridyl)-2-thiabutyl]-7-bromoindole
3-[4-oxo-4-(4-phenyl-1,2,3,6-tetrahydropyridyl)-2-thiabutyl]-5-cyanoindole
3-[4-oxo-4-(4-phenyl-1,2,3,6-tetrahydropyridyl)-2-thiabutyl]-5,6-methylenedioxyindole
3-[4-oxo-4-(4-phenyl-1,2,3,6-tetrahydropyridyl)-2-thiabutyl]-5,6-dimethylindole
3-[4-oxo-4-(4-phenyl-1,2,3,6-tetrahydropyridyl)-2-thiabutyl]-5,6-dimethoxyindole, m.p. 167°–169°
3-[4-oxo-4-(4-phenyl-1,2,3,6-tetrahydropyridyl)-2-thiabutyl]-5,6-dichloroindole
3-[4-oxo-4-(4-o-tolyl-1,2,3,6-tetrahydropyridyl)-2-thiabutyl]indole, m.p. 118°–120°
3-[4-oxo-4-(4-m-tolyl-1,2,3,6-tetrahydropyridyl)-2-thiabutyl]indole, m.p. 98°–101°
3-[4-oxo-4-(4-p-tolyl-1,2,3,6-tetrahydropyridyl)-2-thiabutyl]indole
3-[4-oxo-4-(4-o-methoxyphenyl-1,2,3,6-tetrahydropyridyl)-2-thiabutyl]indole
3-[4-oxo-4-(4-m-methoxyphenyl-1,2,3,6-tetrahydropyridyl)-2-thiabutyl]indole
3-[4-oxo-4-(4-p-methoxyphenyl-1,2,3,6-tetrahydropyridyl)-2-thiabutyl]indole, m.p. 115°–117°
3-[4-oxo-4-(4-o-hydroxyphenyl-1,2,3,6-tetrahydropyridyl)-2-thiabutyl]indole
3-[4-oxo-4-(4-m-hydroxyphenyl-1,2,3,6-tetrahydropyridyl)-2-thiabutyl]indole
3-[4-oxo-4-(4-p-hydroxyphenyl-1,2,3,6-tetrahydropyridyl)-2-thiabutyl]indole
3-[4-oxo-4-(4-o-fluorophenyl-1,2,3,6-tetrahydropyridyl)-2-thiabutyl]indole
3-[4-oxo-4-(4-m-fluorophenyl-1,2,3,6-tetrahydropyridyl)-2-thiabutyl]indole
3-[4-oxo-4-(4-p-fluorophenyl-1,2,3,6-tetrahydropyridyl)-2-thiabutyl]indole, m.p. 130°–131°
3-[4-oxo-4-(4-o-chlorophenyl-1,2,3,6-tetrahydropyridyl)-2-thiabutyl]indole
3-[4-oxo-4-(4-m-chlorophenyl-1,2,3,6-tetrahydropyridyl)-2-thiabutyl]indole
3-[4-oxo-4-(4-p-chlorophenyl-1,2,3,6-tetrahydropyridyl)-2-thiabutyl]indole
3-[4-oxo-4-(4-p-bromophenyl-1,2,3,6-tetrahydropyridyl)-2-thiabutyl]indole
3-[4-oxo-4-(4-m-trifluoromethylphenyl-1,2,3,6-tetrahydropyridyl)-2-thiabutyl]indole, Rf 0.47 ($CH_2Cl_2/CH_3OH$ 95:5)
3-[4-oxo-4-(4-cyanophenyl-1,2,3,6-tetrahydropyridyl)-2-thiabutyl]indole
3-[4-oxo-4-(3,4-methylenedioxyphenyl)-1,2,3,6-tetrahydropyridyl)-2-thiabutyl]indole
3-[4-oxo-4-(4-chloro-3-trifluoromethylphenyl)-1,2,3,6-tetrahydropyridyl)-2-thiabutyl]indole m.p. 124°–125°
3-[4-oxo-4-(4-phenyl-1,2,3,6-tetrahydropyridyl)-2-thiabutyl]indole-S-oxide
3-[4-oxo-4-(4-phenyl-1,2,3,6-tetrahydropyridyl)-2-thiabutyl]indole-S,S-dioxide.

EXAMPLE 5

A mixture of 2.06 g of 3-(4-amino-2-thiabutyl)indole [which may be obtained by reaction of 3-(4-bromo-2-thiabutyl)indole with potassium phthalimide and subsequent hydrolysis] and 2.15 g of 1,5-dichloro-3-phenyl-2-pentene (which may be obtained by reduction of diethyl 3-phenyl-2-penten-1,5-dioate with $LiAlH_4$ and subsequent reaction with $SOCl_2$) in 40 ml of acetone and 40 ml of water is boiled for 24 hours and worked up as usual. "P" of m.p. 109° is obtained.

In analogy, the other compounds of the formula I indicated in Examples 1, 2 and 3 are obtained from the corresponding amines and the corresponding 1,5-dichloro-3-Ar-2-pentenes.

EXAMPLE 6

1 g of $NaBH_4$ in 20 ml of water is added to a solution of 4.25 g of 1-[4-(3-indolyl)-2-thiabutyl]-4-phenylpyridinium bromide [which may be obtained from 3-(4-bromo-2-thiabutyl)indole and 4-phenylpyridine] in 50 ml of 1N NaOH, with stirring, and the mixture is then stirred at 60° for 3 hours. After the usual work-up, "P" of m.p. 109° is obtained.

In analogy, the other compounds of the formula I indicated in Examples 1, 2 and 3 are obtained by reduction of the corresponding pyridinium bromides.

EXAMPLE 7

4.88 g of 1-benzenesulfonyl-3-[4-(4-phenyl-1,2,3,6-tetrahydropyridyl)-2-thiabutyl]indole [which may be obtained from 1-benzenesulfonyl-3-(4-chloro-2-thiabutyl)indole and 4-phenyl-1,2,3,6-tetrahydropyridine] are boiled with 1 g of KOH in 7 ml of water and 14 ml of ethanol for 16 hours, the mixture is concentrated, worked up as usual and "P" of m.p. 109° is obtained.

EXAMPLE 8

2.76 g of Na are dissolved in 180 ml of ethanol, and 21.9 g of 1-(2-mercaptoethyl)-4-phenyl-1,2,3,6-tetrahydropyridine [which may be obtained by reaction of 4-phenyl-1,2,3,6-tetrahydropyridine with thioglycolic acid to give 1-(2-mercaptoacetyl)-4-phenyl-1,2,3,6-tetrahydropyridine and reduction with LiAlH$_4$] and 17.4 g of gramine are added, the mixture is boiled for 16 hours, evaporated, worked up as usual and "P" of m.p. 109° is obtained.

EXAMPLE 9

In analogy to Example 8, 3-[4-(4-phenyl-1,2,3,6-tetrahydropyridyl)-1-thiabutyl]indole hydrochloride of m.p. 191°–193° is obtained from 3-mercaptoindole and 1-(3-bromopropyl)-4-phenyl-1,2,3,6-tetrahydropyridine [which may be obtained by reaction of 3-bromopropionyl bromide with 4-phenyl-1,2,3,6-tetrahydropyridine to give 1-(3-bromopropionyl)-4-phenyl-1,2,3,6-tetrahydropyridine and reduction with LiAlH$_4$].

EXAMPLE 10

3.80 g of 1-methyl-3-[4-(4-hydroxy-4-phenyl-1-piperidyl)-2-thiabutyl]indole [which may be obtained by reaction of 1-methyl-3-(4-bromo-2-thiabutyl)indole with 4-piperidone and subsequent reaction with C$_6$H$_5$Li and hydrolysis] are heated with 40 ml of 1N hydrochloric acid at 50° for 2 hours, worked up as usual and 1-methyl-3-[4-(4-phenyl-1,2,3,6-tetrahydropyridyl)-2-thiabutyl]indole is obtained.

EXAMPLE 11

A solution of 3.62 g of 3-[4-oxo-4-(4-phenyl-1,2,3,6-tetrahydropyridyl)-2-thiabutyl]indole in 10 ml of THF is added dropwise, with stirring, to a suspension of 0.38 g of LiAlH$_4$ in 10 ml of THF. After completion of the reaction, 5 ml of ethyl acetate are added, and the mixture is worked up as usual and "P" of m.p. 109° is obtained.

In analogy, the other compounds of the formula I indicated in Example 1 are obtained from the corresponding amides.

EXAMPLE 12

6 ml of 30% H$_2$O$_2$ are added to a boiling solution of 3.43 g of "P" in 50 ml of ethanol and the mixture is 4 ml of the oxidizing agent, the mixture is boiled a further 9 hours, cooled down, worked up as usual and 3-[4-(4-phenyl-1,2,3,6-tetrahydropyridyl)-2-thiabutyl]indole-S-oxide of m.p. 144°–146° is obtained.

In analogy, the following are obtained by oxidation of the corresponding thioethers:

3-[3-(4-phenyl-1,2,3,6-tetrahydropyridyl)-1-thiapropyl]indole-S-oxide

3-[4-(4-phenyl-1,2,3,6-tetrahydropyridyl)-1-thiabutyl]indole-S-oxide

3-[3-methyl-4-(4-phenyl-1,2,3,6-tetrahydropyridyl)-2-thiabutyl]indole-S-oxide

3-[5-(4-phenyl-1,2,3,6-tetrahydropyridyl)-1-thiapentyl]indole-S-oxide

3-[5-(4-phenyl-1,2,3,6-tetrahydropyridyl)-2-thiapentyl]indole-S-oxide

3-[6-(4-phenyl-1,2,3,6-terahydropyridyl)-2-thiahexyl]indole-S-oxide

3-[4-(4-phenyl-1,2,3,6-tetrahydropyridyl)-2-thiabutyl]-2-methylindole-S-oxide

3-[4-(4-phenyl-1,2,3,6-tetrahydropyridyl)-2-thiabutyl]-5-methoxyindole-S-oxide

3-[4-(4-phenyl-1,2,3,6-tetrahydropyridyl)-2-thiabutyl]-6-methoxyindole-S-oxide

3-[4-(4-phenyl-1,2,3,6-tetrahydropyridyl)-2-thiabutyl]-4-hydroxyindole-S-oxide

3-[4-(4-phenyl-1,2,3,6-tetrahydropyridyl)-2-thiabutyl]-5-hydroxyindole-S-oxide

3-[4-(4-phenyl-1,2,3,6-tetrahydropyridyl)-2-thiabutyl]-6-hydroxyindole-S-oxide

3-[4-(4-phenyl-1,2,3,6-tetrahydropyridyl)-2-thiabutyl]-5-fluoroindole-S-oxide

3-[4-(4-phenyl-1,2,3,6-tetrahydropyridyl)-2-thiabutyl]-5-chloroindole-S-oxide

3-[4-(4-phenyl-1,2,3,6-tetrahydropyridyl)-2-thiabutyl]-7-bromoindole-S-oxide

3-[4-(4-phenyl-1,2,3,6-tetrahydropyridyl)-2-thiabutyl]-5-cyanoindole-S-oxide

3-[4-(4-phenyl-1,2,3,6-tetrahydropyridyl)-2-thiabutyl]-5,6-methylenedioxyindole-S-oxide 3-[4-(4-phenyl-1,2,3,6-tetrahydropyridyl)-2-thiabutyl]-5,6-dimethylindole-S-oxide 3-[4-(4-phenyl-1,2,3,6-tetrahydropyridyl)-2-thiabutyl]-5,6-dimethoxyindole-S-oxide 3-[4-(4-phenyl-1,2,3,6-tetrahydropyridyl)-2-thiabutyl]-5,6-dichloroindole-S-oxide 3-[4-(4-o-tolyl-1,2,3,6-tetrahydropyridyl)-2-thiabutyl]indole-S-oxide 3-[4-(4-m-tolyl-1,2,3,6-tetrahydropyridyl)-2-thiabutyl]indole-S-oxide 3-[4-(4-p-tolyl-1,2,3,6-tetrahydropyridyl)-2-thiabutyl]indole-S-oxide 3-[4-(4-o-methoxyphenyl-1,2,3,6-tetrahydropyridyl)-2-thiabutyl]indole-S-oxide 3-[4-(4-m-methoxyphenyl-1,2,3,6-tetrahydropyridyl)-2-thiabutyl]indole-S-oxide 3-[4-(4-p-methoxyphenyl-1,2,3,6-tetrahydropyridyl)-2-thiabutyl]indole-S-oxide 3-[4-(4-o-hydroxyphenyl-1,2,3,6-tetrahydropyridyl)-2-thiabutyl]indole-S-oxide 3-[4-(4-m-hydroxyphenyl-1,2,3,6-tetrahydropyridyl)-2-thiabutyl]indole-S-oxide 3-[4-(4-p-hydroxyphenyl-1,2,3,6-tetrahydropyridyl)-2-thiabutyl]indole-S-oxide 3-[4-(4-o-fluorophenyl-1,2,3,6-tetrahydropyridyl)-2-thiabutyl]indole-S-oxide 3-[4-(4-m-fluorophenyl-1,2,3,6-tetrahydropyridyl)-2-thiabutyl]indole-S-oxide 3-[4-(4-p-fluorophenyl-1,2,3,6-tetrahydropyridyl)-2-thiabutyl]indole-S-oxide 3-[4-(4-o-chlorophenyl-1,2,3,6-tetrahydropyridyl)-2-thiabutyl]indole-S-oxide 3-[4-(4-m-chlorophenyl-1,2,3,6-tetrahydropyridyl)-2-thiabutyl]indole-S-oxide 3-[4-(4-p-chlorophenyl-1,2,3,6-tetrahydropyridyl)-2-thiabutyl]indole-S-oxide
3-[4-(4-p-bromophenyl-1,2,3,6-tetrahydropyridyl)-2-thiabutyl]indole-S-oxide
3-[4-(4-m-trifluoromethylphenyl-1,2,3,6-tetrahydropyridyl)-2-thiabutyl]indole-S-oxide
3-[4-(4-p-cyanophenyl-1,2,3,6-tetrahydropyridyl)-2-thiabutyl]indole-S-oxide
3-[4-(4-(3,4-methylenedioxyphenyl)-1,2,3,6-tetrahydropyridyl)-2-thiabutyl]indole-S-oxide
3-[4-(4-chloro-3-trifluoromethylphenyl)-1,2,3,6-tetrahydropyridyl)-2-thiabutyl]indole-S-oxide

EXAMPLE 13

9 ml of 30% $H_2O_2$ are added to a solution of 3.48 g of "P" in 20 ml of acetic acid and the mixture is boiled for 90 minutes. After working up as usual, 3-[4-(4-phenyl-1,2,3,6-tetrahydropyridyl)-2-thiabutyl]indole-S,S-dioxide is obtained.

In analogy, the following are obtained by oxidation of the corresponding thioethers:
3-[3-(4-phenyl-1,2,3,6-tetrahydropyridyl)-1-thiapropyl]indole-S,S-dioxide
3-[4-(4-phenyl-1,2,3,6-tetrahydropyridyl)-1-thiabutyl]indole-S,S-dioxide
3-[3-methyl-4-(4-phenyl-1,2,3,6-tetrahydropyridyl)-2-thiabutyl]indole-S,S-dioxide
3-[5-(4-phenyl-1,2,3,6-tetrahydropyridyl)-1-thiapentyl]indole-S,S-dioxide
3-[5-(4-phenyl-1,2,3,6-tetrahydropyridyl)-2-thiapentyl]indole-S,S-dioxide
3-[6-(4-phenyl-1,2,3,6-tetrahydropyridyl)-2-thiahexyl]indole-S,S-dioxide
3-[4-(4-phenyl-1,2,3,6-tetrahydropyridyl)-2-thiabutyl]-2-methylindole-S,S-dioxide
3-[4-(4-phenyl-1,2,3,6-tetrahydropyridyl)-2-thiabutyl]-5-methoxyindole-S,S-dioxide
3-[4-(4-phenyl-1,2,3,6-tetrahydropyridyl)-2-thiabutyl]-6-methoxyindole-S,S-dioxide
3-[4-(4-phenyl-1,2,3,6-tetrahydropyridyl)-2-thiabutyl]-4-hydroxyindole-S,S-dioxide
3-[4-(4-phenyl-1,2,3,6-tetrahydropyridyl)-2-thiabutyl]-5-hydroxyindole-S,S-dioxide
3-[4-(4-phenyl-1,2,3,6-tetrahydropyridyl)-2-thiabutyl]-6-hydroxyindole-S,S-dioxide
3-[4-(4-phenyl-1,2,3,6-tetrahydropyridyl)-2-thiabutyl]-5-fluoroindole-S,S-dioxide
3-[4-(4-phenyl-1,2,3,6-tetrahydropyridyl)-2-thiabutyl]-5-chloroindole-S,S-dioxide
3-[4-(4-phenyl-1,2,3,6-tetrahydropyridyl)-2-thiabutyl]-7-bromoindole-S,S-dioxide
3-[4-(4-phenyl-1,2,3,6-tetrahydropyridyl)-2-thiabutyl]-5-cyanoindole-S,S-dioxide
3-[4-(4-phenyl-1,2,3,6-tetrahydropyridyl)-2-thiabutyl]-5,6-methylenedioxyindole-S,S-dioxide
3-[4-(4-phenyl-1,2,3,6-tetrahydropyridyl)-2-thiabutyl]-5,6-dimethylindole-S,S-dioxide
3-[4-(4-phenyl-1,2,3,6-tetrahydropyridyl)-2-thiabutyl]-5,6-dimethoxyindole-S,S-dioxide
3-[4-(4-phenyl-1,2,3,6-tetrahydropyridyl)-2-thiabutyl]-5,6-dichloroindole-S,S-dioxide
3-[4-(4-o-tolyl-1,2,3,6-tetrahydropyridyl)-2-thiabutyl]indole-S,S-dioxide
3-[4-(4-m-tolyl-1,2,3,6-tetrahydropyridyl)-2-thiabutyl]indole-S,S-dioxide
3-[4-(4-p-tolyl-1,2,3,6-tetrahydropyridyl)-2-thiabutyl]indole-S,S-dioxide
3-[4-(4-o-methoxyphenyl-1,2,3,6-tetrahydropyridyl)-2-thiabutyl]indole-S,S-dioxide
3-[4-(4-m-methoxyphenyl-1,2,3,6-tetrahydropyridyl)-2-thiabutyl]indole-S,S-dioxide
3-[4-(4-p-methoxyphenyl-1,2,3,6-tetrahydropyridyl)-2-thiabutyl]indole-S,S-dioxide
3-[4-(4-o-hydroxyphenyl-1,2,3,6-tetrahydropyridyl)-2-thiabutyl]indole-S,S-dioxide
3-[4-(4-m-hydroxyphenyl-1,2,3,6-tetrahydropyridyl)-2-thiabutyl]indole-S,S-dioxide
3-[4-(4-p-hydroxyphenyl-1,2,3,6-tetrahydropyridyl)-2-thiabutyl]indole-S,S-dioxide
3-[4-(4-o-fluorophenyl-1,2,3,6-tetrahydropyridyl)-2-thiabutyl]indole-S,S-dioxide
3-[4-(4-m-fluorophenyl-1,2,3,6-tetrahydropyridyl)-2-thiabutyl]indole-S,S-dioxide
3-[4-(4-p-fluorophenyl-1,2,3,6-tetrahydropyridyl)-2-thiabutyl]indole-S,S-dioxide
3-[4-(4-o-chlorophenyl-1,2,3,6-tetrahydropyridyl)-2-thiabutyl]indole-S,S-dioxide
3-[4-(4-m-chlorophenyl-1,2,3,6-tetrahydropyridyl)-2-thiabutyl]indole-S,S-dioxide
3-[4-(4-p-chlorophenyl-1,2,3,6-tetrahydropyridyl)-2-thiabutyl]indole-S,S-dioxide
3-[4-(4-p-bromophenyl-1,2,3,6-tetrahydropyridyl)-2-thiabutyl]indole-S,S-dioxide
3-[4-(4-m-trifluoromethylphenyl-1,2,3,6-tetrahydropyridyl)-2-thiabutyl]indole-S,S-dioxide
3-[4-(4-p-cyanophenyl-1,2,3,6-tetrahydropyridyl)-2-thiabutyl]indole-S,S-dioxide
3-[4(4-(3,4-methylenedioxyphenyl)-1,2,3,6-tetrahydropyridyl)-2-thiabutyl]indole-S,S-dioxide
3-[4-(4-(4-chloro-3-trifluoromethylphenyl)-1,2,3,6-tetrahydropyridyl)-2-thiabutyl]indole-S,S-dioxide

EXAMPLE 14

A mixture of 4.25 g of 3-[4-(4-p-methoxyphenyl-1,2,3,6-tetrahydropyridyl)-2-thiabutyl]indole hydrochloride and 3.5 g of pyridine hydrochloride is stirred at 160° for 3 hours. After working up as usual, 3-[4-(4-p-hydroxyphenyl-1,2,3,6-tetrahydropyridyl)-2-thiabutyl]indole is obtained.

The examples below relate to pharmaceutical formulations containing amines of the formula I or their acid addition salts:

EXAMPLE A

Tablets

A mixture of 1 kg of 3-[4-(4-phenyl-1,2,3,6-tetrahydropyridyl)-2-thiabutyl]indole, 4 kg of lactose, 1.2 kg of potato starch, 0.2 kg of talc and 0.1 kg of magnesium stearate is compressed to form tablets in a customary manner such that each tablet contains 10 mg of active compound.

EXAMPLE B

Coated tablets

Tablets are formed by compression in analogy to Example A and these are then coated in a customary manner with a coating of sucrose, potato starch, talc, tragacanth and dyestuff.

EXAMPLE C

Capsules 2 kg of 3-[4-(4-phenyl-1,2,3,6-tetrahydropyridyl)-2-thiabutyl]indole are filled into hard gelatine capsules in a customary manner such that each capsule contains 20 mg of the active compound.

EXAMPLE D

Ampoules

A solution of 1 kg of 3-[4-(4-phenyl-1,2,3,6-tetrahydropyridyl)-1-thiabutyl]indole hydrochloride in 30 liters of double distilled water is sterilized by filtration, filled into ampoules, freeze-dried under sterile conditions and closed sterile. Each ampoule contains 10 mg of active compound.

In analogy, tablets, coated tablets, capsules and ampoules can be obtained which contain one or more of the other active compounds of the formula I and/or their physiologically acceptable acid addition salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sulfur-containing indole derivative of the formula

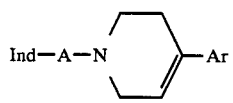

wherein

Ind is 3-indolyl or 3-indolyl substituted once or twice by alkyl, O-alkyl, S-alkyl, SO-alkyl, $SO_2$-alkyl, OH, F, Cl, Br, $CF_3$ or CN or by methylenedioxy;

A is $-(CH_2)_n-E-C_mH_{2m}-$ or $-(CH_2)_n-E-C_{m-1}H_{2m-2}CO-$;

n is 0 or 1;

m is 2, 3 or 4;

E is S, SO or $SO_2$;

and

Ar is phenyl or phenyl substituted once or twice by alkyl, O-alkyl, S-alkyl, SO-alkyl, $SO_2$-alkyl, OH, F, Cl, Br, $CF_3$ or CN or by methylenedioxy;

wherein each alkyl group is of 1-4C atoms;

or a physiologically acceptable acid addition salt thereof.

2. A compound of claim 1 wherein Ind is 3-indolyl and Ar is phenyl.

3. A compound of claim 1 wherein alkyl is methyl.

4. A compound of claim 1 wherein Ind is 3-indolyl monosubstituted in the 2-, 5- or 6-position by methyl, ethyl, methoxy, ethoxy, methylthio, ethylthio, OH, F, Cl, Br, $CF_3$ or CN.

5. A compound of claim 1 wherein n is 1, m is 2 and E is S.

6. A compound of claim 1 wherein A is straight-chained.

7. A compound of claim 1 wherein A is $-CH_2-E-CH_2CH_2-$ or $-CH_2-E-CH_2-CO-$.

8. A compound of claim 1 wherein Ar is phenyl monosubstituted by methyl, F, Cl, Br or trifluoromethyl.

9. A compound of claim 1 wherein Ind is 3-indoyl, methyl-3-indolyl, dimethyl-3-indolyl, methoxy-3-indolyl, dimethoxy-3-indolyl, hydroxy-3-indolyl, dihydroxy-3-indolyl, fluoro-3-indolyl, chloro-3-indolyl, dichloro-3-indolyl, bromo-3-indolyl, cyano-3-indolyl or methylenedioxy-3-indolyl, the substituents being in the 5- or 6-position.

10. A compound of claim 1 wherein Ind is 3-indolyl, 5- or 6-methyl-3-indolyl, 5,6-dimethyl-3-indolyl, 5- or 6-methoxy-3-indolyl, 5,6-dimethoxy-3-indolyl, 5- or 6-hydroxy-3-indolyl or 5-cyano-3-indolyl.

11. A compound of claim 1 wherein Ind is 3-indolyl, 5-methoxy-3-indolyl, or 5-hydroxy-3-indolyl, A is $-S-CH_2CH_2-$, $-S-CH_2-CO-$, $-S-(CH_2)_3-$, $-S-CH_2CH_2-CO-$, $-CH_2-S-CH_2CH_2-$, $-CH_2-S-CH_2-CO-$, $-CH_2-SO-CH_2CH_2-$, $-CH_2-S-(CH_2)_3-$ or $-CH_2-S-CH_2CH_2-CO-$ and Ar is phenyl, tolyl, methoxyphenyl, fluorophenyl, chlorophenyl, trifluoromethylphenyl or chlorotrifluoromethylphenyl.

12. A compound of claim 1 wherein Ind is 3-indolyl, A is $-(CH_2)_n-E-C_mH_{2m}-$, m is 2 or 3 and Ar is phenyl.

13. A compound of claim 1 wherein Ind is 3-indolyl, A is $-S-CH_2CH_2-$, $-S-(CH_2)_3-$, $-CH_2-S-CH_2CH_2-$, $-CH_2SO-CH_2CH_2-$ or $-CH_2-S-(CH_2)_3$ and Ar is phenyl.

14. A compound of claim 1 wherein Ind is 3-indolyl, A is $-CH_2-E-CH_2CH_2-$ or $-CH_2-E-CH_2CO-$ and Ar is phenyl.

15. 3-[4-(4-phenyl-1,2,3,6-tetrahydropyridyl)-2-thiabutyl]indole, a compound of claim 1.

16. A pharmaceutical composition comprising a compound of claim 1 effective to treat parkinsonism, extrapyramidal side effects in neuroleptic therapy, depression or schizophrenia and a pharmaceutically acceptable carrier.

17. A method of treating Parkinsonism comprising administering to a patient an effective amount of a compound of claim 1.

18. A method of treating extrapyramidal side effects in neuroleptic therapy comprising administering to a patient an effective amount of a compound of claim 1.

19. A method of treating depression comprising administering to a patient an effective amount of a compound of claim 1.

20. A method of treating schizophrenia comprising administering to a patient an effective amount of a compound of claim 1.

21. A pharmaceutical composition according to claim 16 containing between about 0.2 and 500 mg of said compound.

* * * * *